(12) United States Patent
Kolt

(10) Patent No.: US 8,602,960 B2
(45) Date of Patent: Dec. 10, 2013

(54) K-RING ELECTROMAGNETIC TREATMENT APPARATUS, SYSTEM AND METHOD FOR TUMORS, ARTHRITIS AND OTHER AILMENTS

(76) Inventor: Stanley Kolt, Mamaroneck, NY (US)

( * ) Notice: Subject to any disclaimer, the term of this patent is extended or adjusted under 35 U.S.C. 154(b) by 413 days.

(21) Appl. No.: 12/958,673

(22) Filed: Dec. 2, 2010

(65) Prior Publication Data

US 2011/0077452 A1    Mar. 31, 2011

Related U.S. Application Data

(63) Continuation-in-part of application No. 11/551,011, filed on Oct. 19, 2006, now abandoned.

(51) Int. Cl.
*A61N 2/02* (2006.01)

(52) U.S. Cl.
USPC ............................................. 600/13

(58) Field of Classification Search
USPC ................... 600/9–15; 606/32–52
See application file for complete search history.

(56) References Cited

U.S. PATENT DOCUMENTS

| | | | |
|---|---|---|---|
| 3,915,151 A | 10/1975 | Kraus | |
| 4,527,550 A | 7/1985 | Ruggera | |
| 5,084,003 A * | 1/1992 | Susic | 600/13 |
| 5,131,904 A | 7/1992 | Markoll | |
| 5,181,902 A | 1/1993 | Erickson et al. | |
| 5,518,495 A * | 5/1996 | Kolt | 600/13 |
| 5,570,021 A | 10/1996 | Dachniwskyj | |
| 6,083,149 A | 7/2000 | Wascher et al. | |
| 6,149,577 A * | 11/2000 | Bouldin et al. | 600/13 |
| 6,272,370 B1 | 8/2001 | Gillies et al. | |
| 6,309,340 B1 * | 10/2001 | Nakagawa | 600/14 |
| 6,592,509 B1 | 7/2003 | Hunter | |
| 2001/0018547 A1 * | 8/2001 | Mechlenburg et al. | 600/15 |

* cited by examiner

Primary Examiner — Charles A Marmor, II
Assistant Examiner — Catherine E Burk
(74) Attorney, Agent, or Firm — Heslin Rothenberg Farley & Mesiti, P.C.

(57) ABSTRACT

A magnetic field therapy apparatus includes a first wire coil, a second wire coil and an electrically conductive member connecting the coils in series. The coils are wound in the same direction. In a preferred embodiment the coils are wrapped around a single bobbin, with the first coil forming a bottom layer and the second coil wrapped around the first coil and forming a top layer. AC power coupled to the coils energizes the coils and generates a magnetic field within the bobbin interior region. When current enters one coil it induces current in the other coil, thereby creating a scalar effect, producing energy in the form of a helix. The waves are identical, but out of phase temporally, that is, physically identical, but 180 degrees out of phase in terms of time. In an alternate embodiment, the coils may be on separate bobbins. A trigger may be applied to the part of a body undergoing therapy.

22 Claims, 11 Drawing Sheets

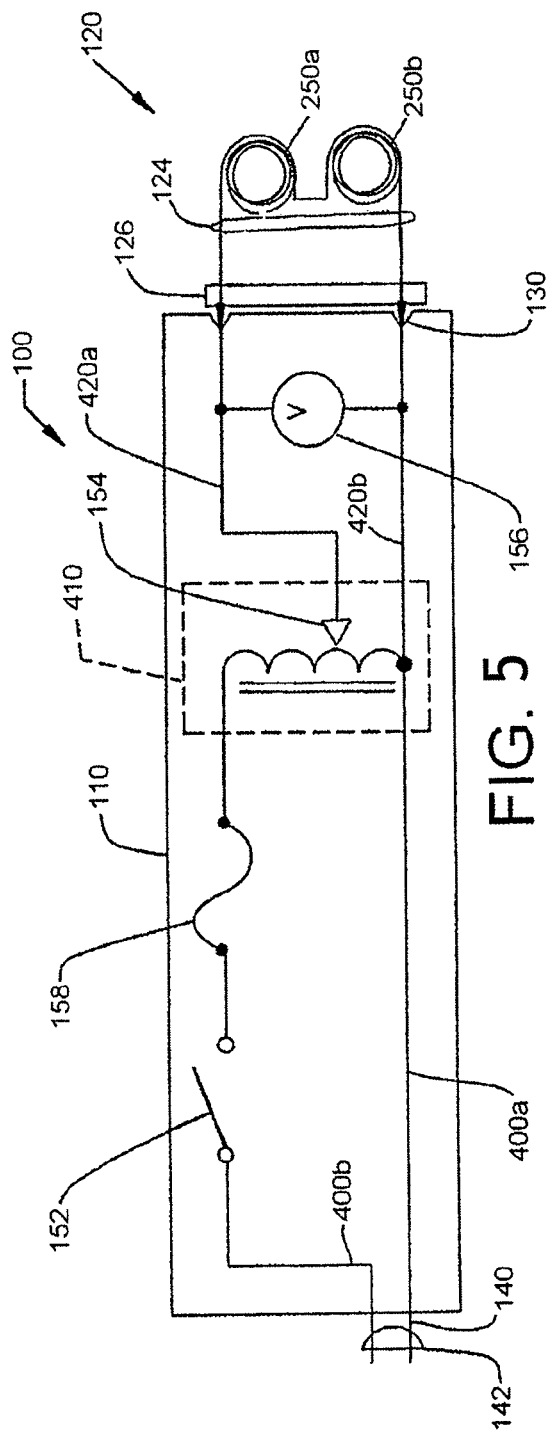
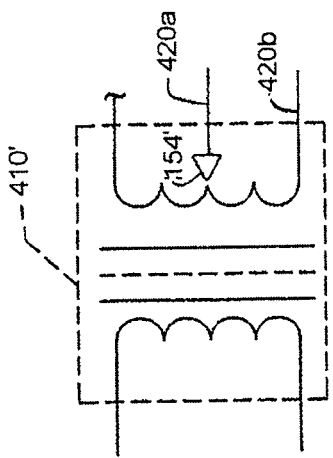
FIG. 5
FIG. 6

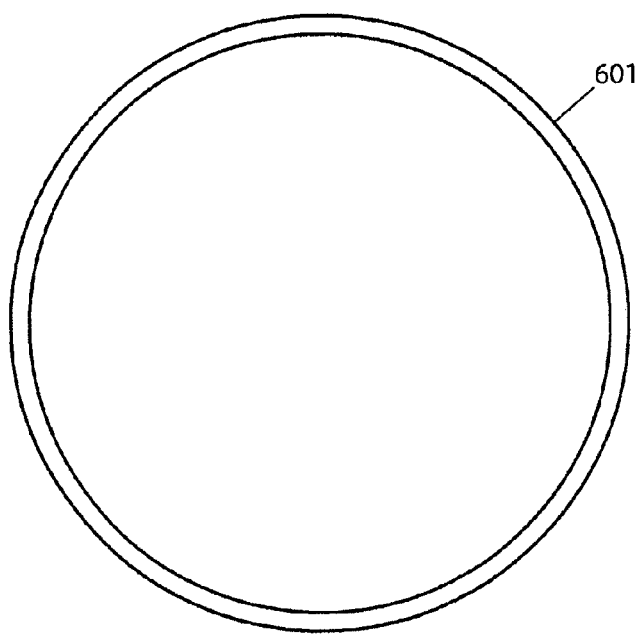
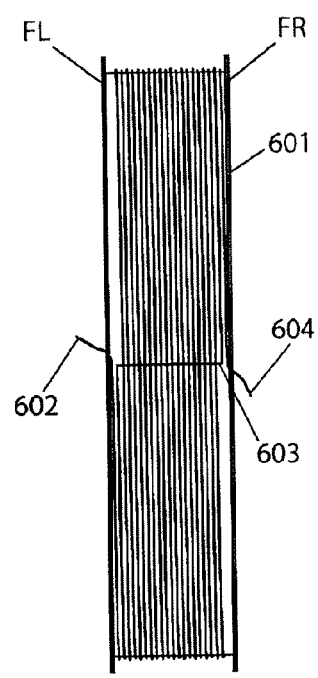
FIG 8  FIG 9

SECTION B-B

K-RING ELECTROMAGNETIC TREATMENT APPARATUS, SYSTEM AND METHOD FOR TUMORS, ARTHRITIS AND OTHER AILMENTS

CROSS-REFERENCE TO RELATED APPLICATION

The present application is a Continuation-in-Part of my Non-Provisional application Ser. No. 11/551,011 filed Oct. 19, 2006. This prior application is incorporated herein by this reference and the benefit of its filing date is claimed herein as well.

FIELD OF THE INVENTION

The present invention relates generally to a magnetic field therapy apparatus for treating or at least giving relief to biological subjects such as mammals who suffer from tumors, arthritis and other ailments and, more particularly, to a portable alternating current (AC) electromagnetic field source apparatus, system and method adapted to receive portions of a biological subject within the hollow of an enclosure generating a magnetic field.

BACKGROUND

The use of electromagnetic energy as a therapeutic aid for various types of ailments is documented in the art. For example, U.S. Pat. No. 5,518,495, issued May 21, 1996 to Kolt discloses a magnetic field therapy apparatus wherein a single coil is connected to a source of commercially available AC power, illustratively, 120 volts at 60 Hertz, for applying the resulting magnetic field to an appendage of a human being as well as body portions thereof.

Such a configuration, however, generates an electromagnetic field with a comparatively lower frequency and energy while using a comparatively higher current or power to operate. In many circumstances, the prior art is generally related to non-portable devices and thus require an individual to travel to a doctor's or therapist's office since the patient is unable to utilize the equipment from home. Typically, a DC source is utilized to create the resulting magnetic field instead of a commercially available AC power source. Even where a commercially available AC power source is used, the magnetic field strength at a desired point is limited to the 60 Hertz cycle. The source of AC current may further be connected to a transformer to vary the resulting voltage, but it will still exhibit the 60 Hertz cycle. Such devices are often complicated to operate and expensive to manufacture. Accordingly, the prior art has not taken into account the beneficial effects of a lightweight portable apparatus that is reliable, inexpensive and suitable for treating or at least giving relief to biological subjects who suffer from tumors, arthritis and other ailments utilizing an AC power source to create a magnetic field derived from a frequency greater than 60 Hertz.

These and other deficiencies were solved by increasing the number of coils from a singular coil to two concentric electrically connected coils. Two concentrically electrically connected coils have the benefit of substantially doubling the frequency, nearly halving the requisite amperage with a minimal increase in voltage. Further, a somewhat rigid non-conductive material such as epoxy, or the like, may be placed between the two concentric coils to maintain a substantially constant distance between them to assist in creating a more uniform electromagnetic field. Additionally, a trigger at least partially constructed of a magnet, electrically conductive material, or the like, may be worn by a biological subject brought within proximity of or near the two-coils to influence the generated electromagnet field to the trigger area.

SUMMARY

Various embodiments are provided herein which address among other things the increased electromagnetic field generated by at least two concentric electrically connected coils, and so forth.

In accordance with an embodiment, a magnetic field therapy apparatus includes first and second concentric electrically connected coils of wire wherein the innermost region is hollow and an AC power unit coupled to the coils for energizing them. A wearable trigger may then be brought into close proximity to the energized coils to direct the electromagnetic field through a treatment area. The concentrically positioned coils, hereinafter "K-Ring", substantially increase the energy and frequency of the generated electromagnetic field and substantially reduce the amperage or power needed to generate such a high energy electromagnetic field compared to conventional single coil configurations.

In accordance with a further embodiment, a method of treating tumors and relieving arthritis pain and other ailments includes the steps of configuring a first and second concentric electrically connected coils of wire; energizing the coils; generating an AC electromagnetic field; placing a biological subject in the AC electromagnetic field and exposing the biological subject to said AC electromagnetic field with or without a trigger.

BRIEF DESCRIPTION OF THE DRAWINGS

In the drawings, like reference numbers generally indicate identical, functionally similar, and/or structurally similar elements. The various exemplary embodiments will be described with reference to the accompanying drawings, wherein:

FIG. 5 is a schematic diagram of the electrical components of the present invention in accordance with an embodiment; and FIG. 6 is an alternative schematic diagram of the voltage adjuster block in accordance with an embodiment.

FIG. 8 is a front view of a preferred alternate embodiment of the present invention showing a single bobbin holding a pair of wire coils.

FIG. 9 is a side view of the bobbin of FIG. 8 and showing the wire leads to the coils.

DETAILED DESCRIPTION OF THE VARIOUS EMBODIMENTS

Figure 1:
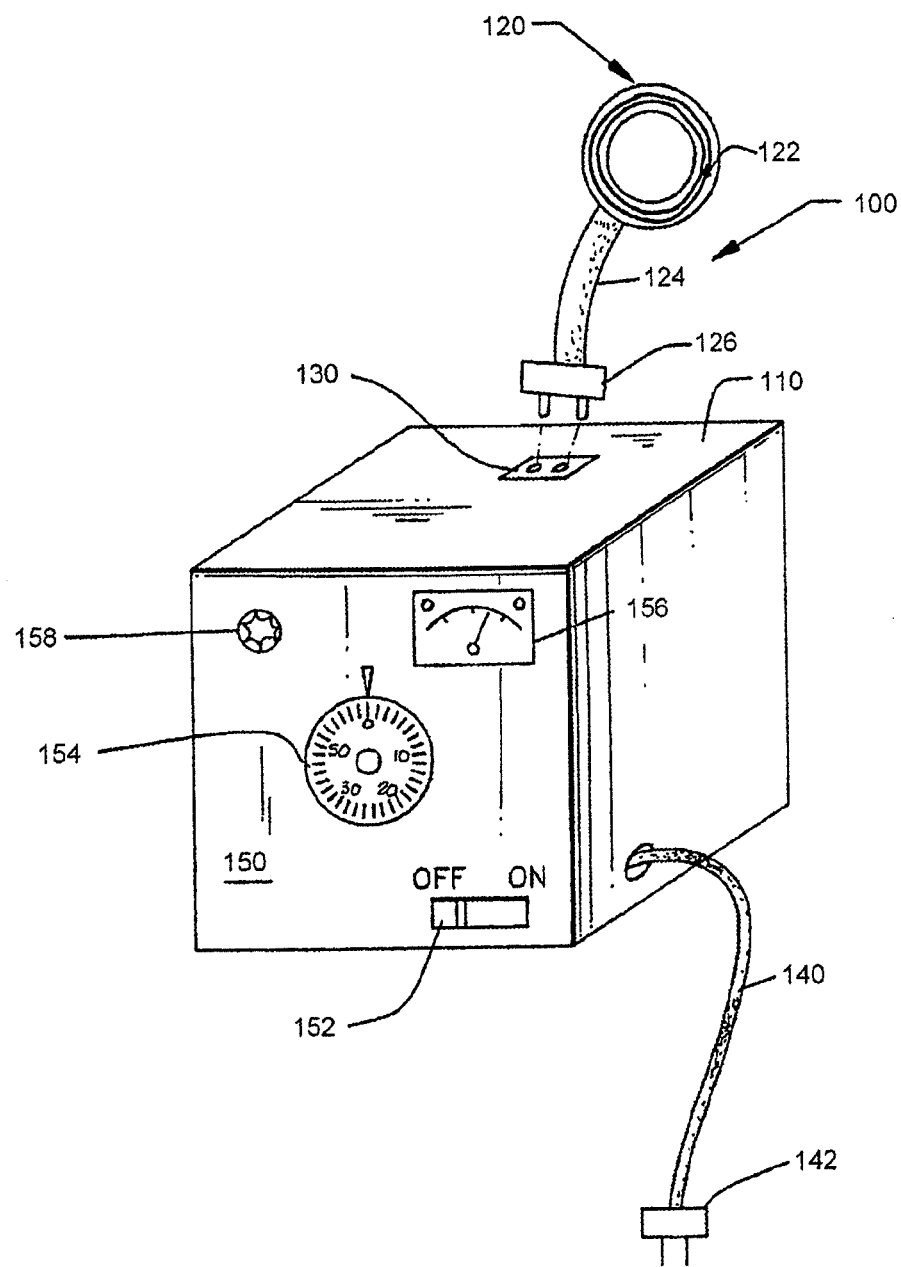
FIG. 1 is a perspective frontal view of an exemplary apparatus in accordance with an embodiment.

FIG. 1 is a perspective frontal view of an exemplary apparatus device 100 in accordance with an embodiment. As shown, in this example, apparatus 100 includes an enclosure (or housing) 110 containing circuitry connectable between a source of commercially available AC power and a K-Ring magnetic field generator 120. K-Ring 120 is enclosed within an insulative toroidal housing and includes at least two coils denominated by double-ring lines 122. K-Ring 120 is connected to the circuitry within the housing 110 by cable(s) 124 terminated by connector 126 adapted, arranged in or associated for receipt by a socket(s) interface 130 mounted to housing 110 or to other structures. The circuitry within housing 110 is connected to commercially available AC power (i.e., a standard wall outlet) by cable 140 terminated by standard wall outlet male-plug 142.

Anterior panel 150 of housing 110 has mounted thereto on/off switch 152, control dial 154, meter display 156 and overcurrent protection device 158, such as a fuse, circuit breaker or the like.

Figure 2:
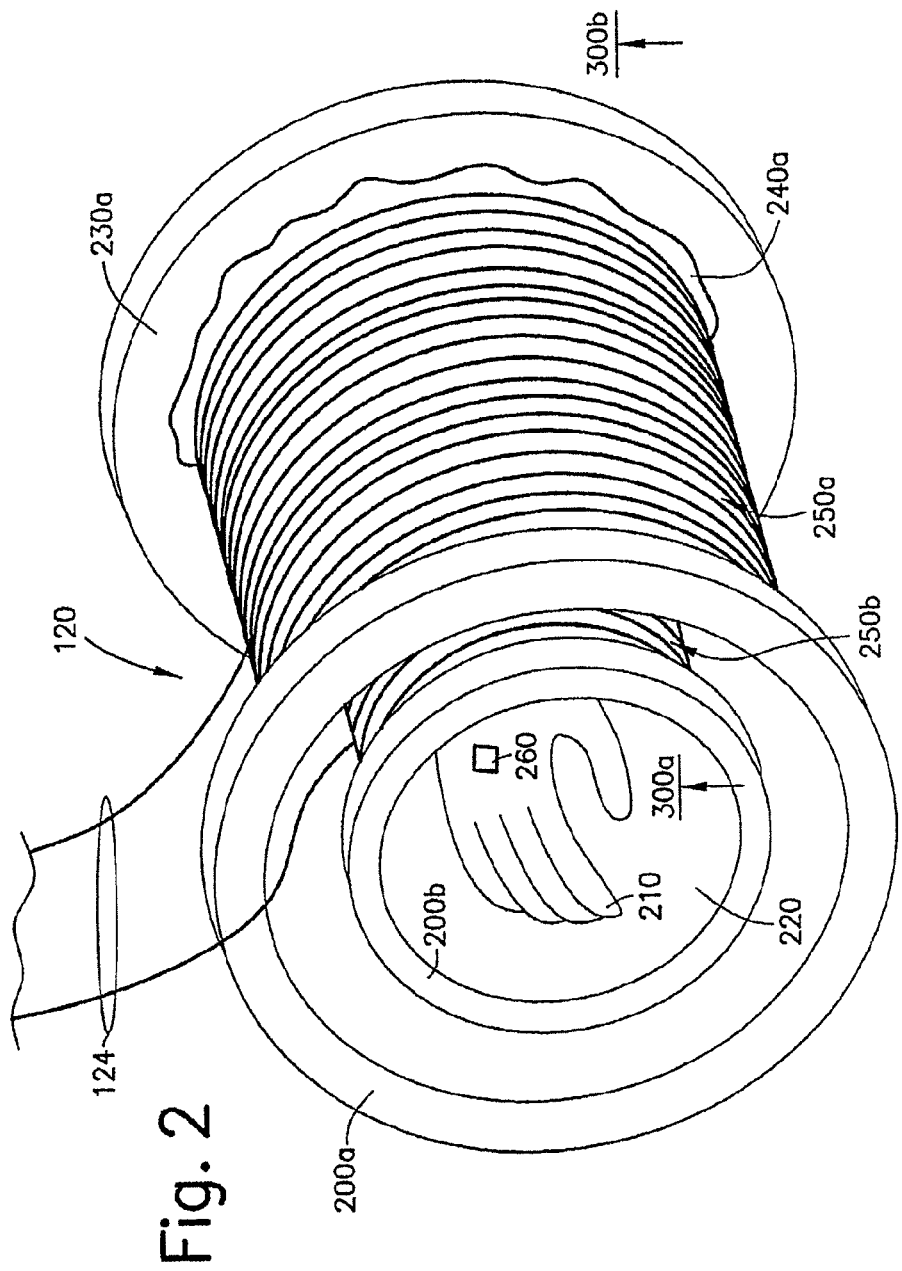
FIG. 2 is a perspective frontal view of an exemplary magnetic field generator including a second bobbin concentrically confining a first bobbin in accordance with an embodiment.

FIG. 2 is a perspective frontal view of an exemplary magnetic field generator in accordance with an embodiment. As shown, in this example, K-Ring 120, without insulative housing 122, includes first bobbin 200a and second bobbin 200b each formed of non-magnetic material such as copper, its alloys (e.g., brass, bronze, or other alloys) or other suitable non-magnetic materials. A first area defined by the confined area of the interior circumference of first bobbin 200a and the exterior circumference of second bobbin 200b is preferably a distance of 4% or less from the interior circumference of first bobbin 200a and the outer circumference of second bobbin 200b—the 4% number being measured as the difference between the lengths of the interior circumference of first bobbin 200a and exterior circumference of second bobbin 200b. This minimum distance may be maintained by utilizing an epoxy, rubber, polyvinyl chloride, neoprene or other insulation material between first bobbin 200a and second bobbin 200b. The inner bobbin 200b has inner central opening 220 adapted to receive a portion of biological subject 210 therein.

A temporarily fastenable magnetic trigger 260 is placed on or near the biological subject portion to further influence the resulting magnetic field. Trigger 260 is preferably encased in bronze or copper. Trigger 260 is preferably positioned on an opposite side of a subject from its treatment area so that the magnetic flux generated by the K-Ring passes through the treatment area to the trigger. A preferred trigger has the following dimensions: three and one half to four inches in diameter and two inches thick. Such magnetic trigger 260 may be fastened via an adhesive, or the like to the subject.

The biological subject portion receivable within opening 220 depends on the size of opening 220. By way of example, if the diameter of opening 220 is on the order of six inches, the biological subject portion receivable within such opening 220 may be a hand 210, as shown by the broken line representation thereof, or the like. Opening 220 may be configured to treat any biological subject, involving animals such as a horse, dog, cat, or any other animal.

Figure 3:
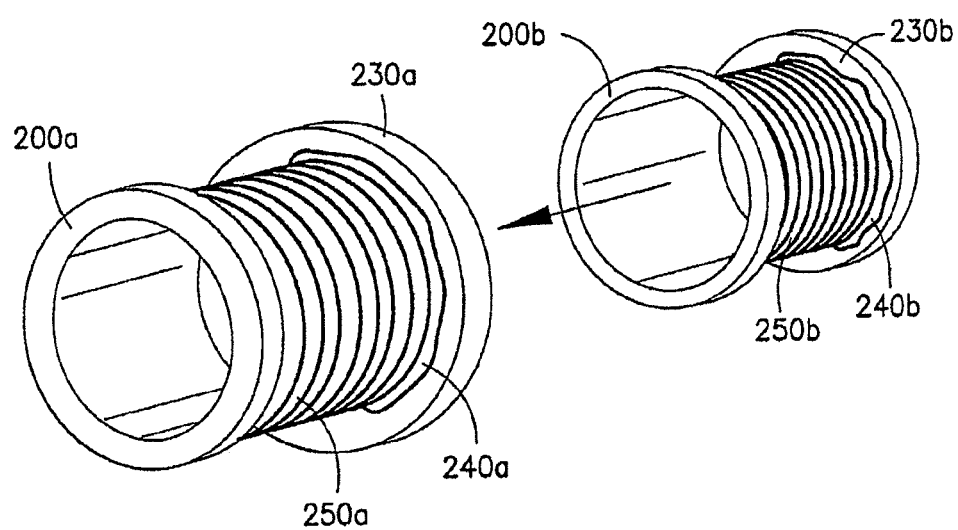
FIG. 3 is a perspective frontal view of a first and second bobbin prior to insertion of said first bobbin concentrically within said second bobbin.

FIG. 3 is a perspective frontal view of said first and second bobbins prior to insertion of said first bobbin concentrically within said second bobbin to form said K-Ring 120. As shown in more detail in FIG. 3, each bobbin 200a, 200b is configured to include an outer channel 230a, 230b lined with a sheet of cloth material 240a, 240b, preferably linen, or other material suitable for lining the outer channel. A length of electrically conductive insulated wire(s) 250a is first wound around first bobbin 200a over the cloth 240a and within channel 230a so as to form a first coil. Second bobbin 200b is similarly wound by a length of electrically conductive insulated wire(s) 250b over cloth 240b and within channel 230b so as to form a second coil wherein electrically conductive insulated wire(s) 250a, 250b may be a single length or composed of at least two electrically connected wires. Wire(s) 250a, 250b is terminated in cable 124 connected to the connector 126.

The diameter of wire(s) 250a, 250b and the number of turns forming a coil wound around the bobbins 200a, 200b is determined by their respective radii, distance between outer channels 230a, 230b as well as desired heat generation restraints. The resulting magnetic flux density generated by K-Ring 120 is desired to be within a certain range, as will be discussed hereinafter.

Figure 4:
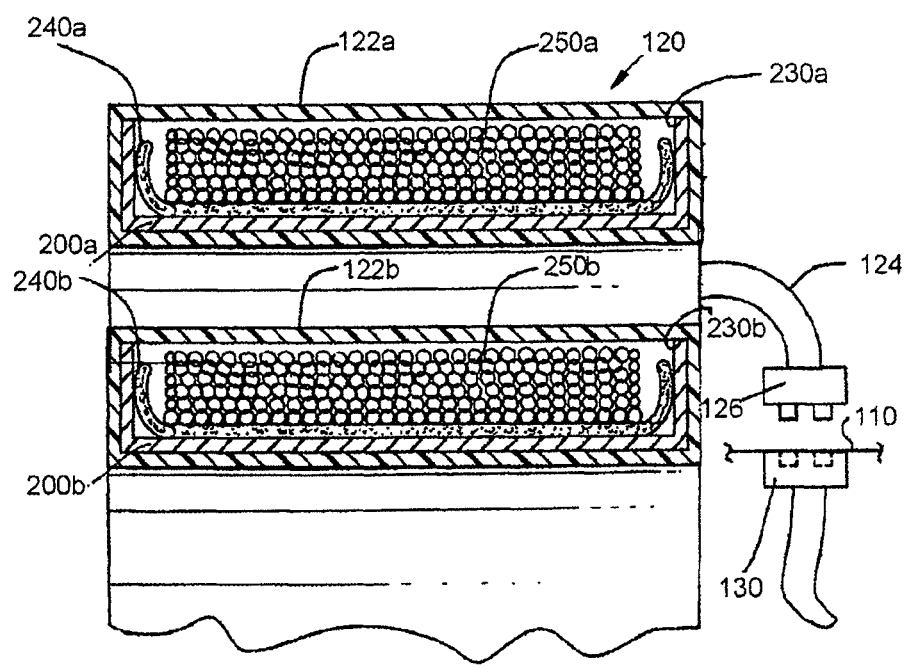
FIG. 4 is a cross-sectional view of an exemplary magnetic field generator along the line defined by reference character 300a-300b in FIG. 2 in accordance with an embodiment.

FIG. 4 is a cross-sectional view of an exemplary magnetic field generator along the line defined by reference character 300a-300b in FIG. 2 in accordance with an embodiment. After wire(s) 250a, 250b is wound on each bobbin 200a, 200b, an insulative toroidal housing, or cover, or the like, 122a and 122b, preferably formed of a plastic material, is placed over each bobbin 200a, 200b individually and/or collectively after wire(s) 250a, 250b is wound to folin the coils to shield wire(s) 250a, 250b from the environment and prevent it from absorbing moisture, which might effect its operation. Further, an epoxy, rubber, polyvinyl chloride, neoprene or other insulation material may be utilized between first bobbin 200a and second bobbin 200b to maintain a substantially uniform separation distance. In this embodiment, bobbins 250a and 250b each have a plurality of coil layers. Any number of coil layers are suitable for use in the K-Ring, including a single coil layer in each bobbin.

FIG. 5 is a schematic diagram of the electrical components contained within housing 110 of the present invention in accordance with an embodiment. As shown, male-plug 142 is a conventional wall plug adapted for insertion into a wall outlet connected to a source of commercially available AC power, for example, 120 volts at 60 Hertz. Plug 142 is connected by cable 140 to conductors 400a, 400b within housing 110 and thereby to the input of voltage adjuster 410. In series with conductor 400b is on/off switch 152 and overcurrent protection device 158. Illustratively, voltage adjuster 410 on conductors 420a, 420b is connected to socket 130. Voltmeter 156, whose display is visible through anterior panel 150 of housing 110, is connected across conductors 420a, 420b. Plug 126 of magnetic field generator 120 is insertable into socket 130 to complete the circuit.

An alternative construction for voltage adjuster 410 is shown in FIG. 6 and designated by reference number 410'. In this alternative construction, voltage adjuster 410' is a step down transformer having a variable tap 154' on its secondary winding, which is connected to output conductors 420a, 420b. The arrangement shown in FIG. 6 isolates magnetic field generator 120 from input plug 142 to provide further protection to the user of the device.

By applying alternative current to wire(s) 250a, 250b forming the coils of magnetic field generator 120, a magnetic field is generated within central opening 220. This field is strongest at the outer periphery of inner bobbin 200b of opening 220 and decreases towards its center. The K-Ring configuration doubles the frequency, for example, from 60 Hertz to 120 Hertz, while utilizing less amperage (e.g., about 40% less amperage) of conventional single ring magnetic field therapy apparatuses. The maximum magnetic flux density varies depending upon positioning of the trigger and desired treatment results. To achieve that field, an output voltage from voltage adjuster 410 is in the range from about 6 volts to about 24 volts wherein the current will range from about 1 amp to 10 amps, preferably 1-5 amps. It is understood that the number of turns of wire(s) 250a, 250b forming each of the two coils is a factor in the strength of the magnetic field. Each coil may be configured to receive small and large gauge wires, having a preferable range between 14 and 19. The size, number of turns and configuration of wire(s) 250a, 250b and contact(s) may be varied as desired depending on the type of wires and the application for K-Ring 120. Experiments with various materials for the bobbins 200a, 200b resulted in a selection of copper or its alloys (e.g., brass or bronze) as the materials of choice. It is believed that copper, brass or bronze bobbins, through the eddy currents induced therein by the varying magnetic field, has a filter effect on the magnetic field which promotes the therapeutic benefits produced by the inventive apparatus.

Figure 7:
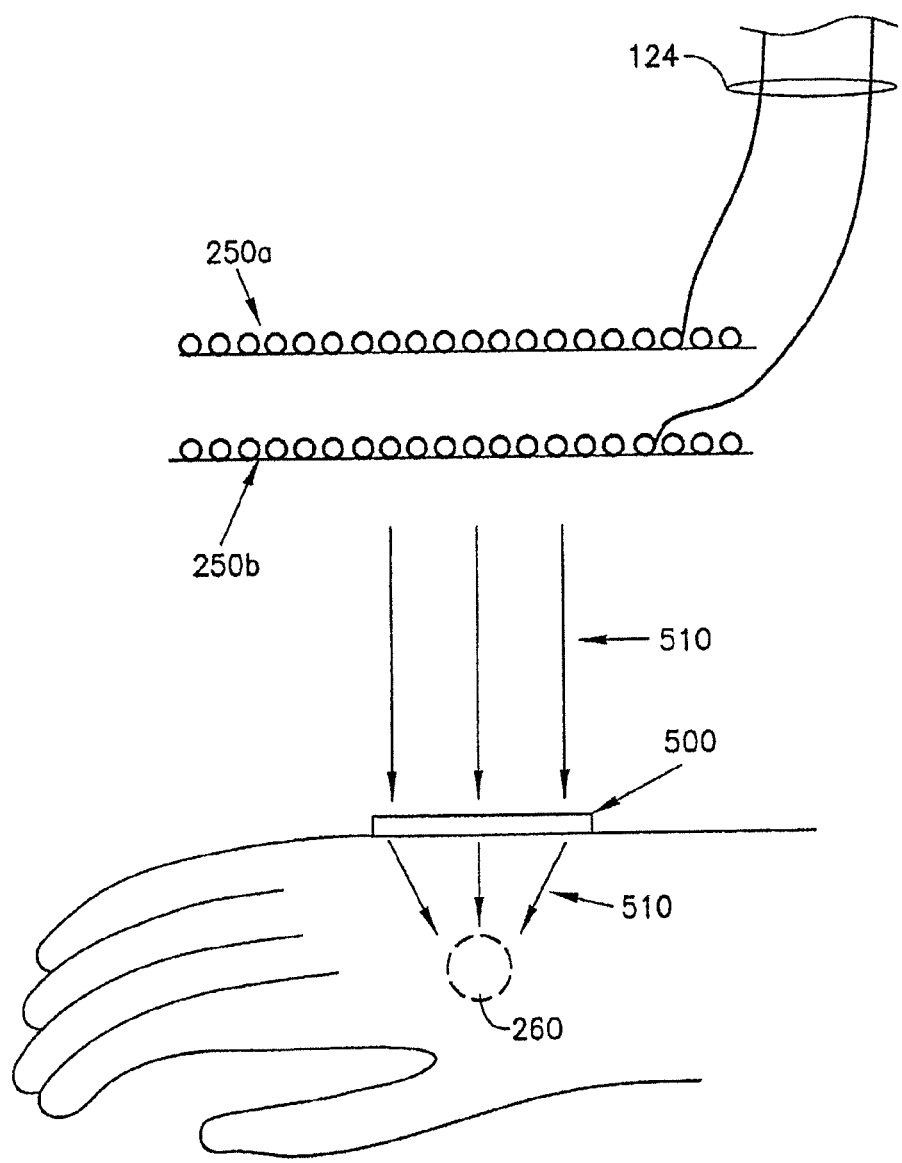
FIG. 7 is a schematic of the magnetic flux generated by the K-Ring passing through a treatment area to the magnetic trigger.
Figure 10:
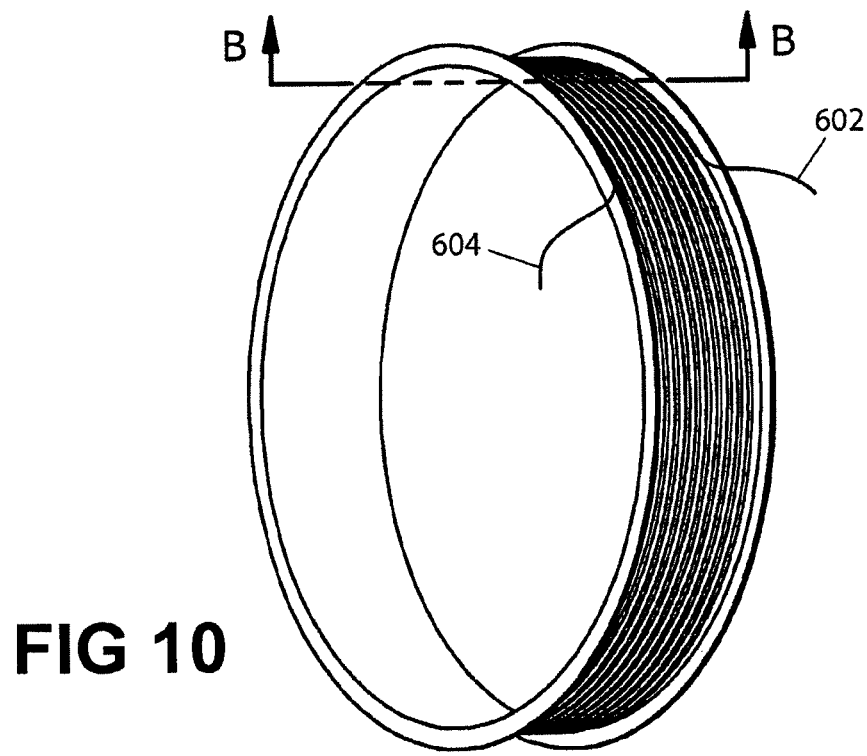
FIG. 10 is a perspective view of the bobbin of FIGS. 8 and 9.

FIG. 7 is an exemplary illustration of a K-Ring, having single coil layer bobbins 250a and 250b, generating magnetic flux 510 through treatment area 500 to trigger 260. In this embodiment, trigger 260 is positioned on the opposite side, or palm of the subject hand from the treatment area located on the top portion of the hand.

Although the K-Ring 120 is described above as having two bobbins 200a, 200b (e.g., 2 coils), the K-Ring 120 may include any number of bobbins and coils as desired. Various characteristics of the K-Ring may also be varied. For example, the size and shape (for example, substantially circular or elliptical) and material of the components (e.g., bobbins, insulating materials or connectors) may be suitably selected and configured depending on the application. For example, voltage adjuster 410 may have its selectable range (e.g., 1-20 V, 5-40) limited, such as through use of the combination of known electrical components.

Referring now to FIGS. 8-11, an alternate, preferred embodiment of the present invention is shown. There is shown a single bobbin 601 with flanges FL and FR. A first length of electrically conductive insulative wire is wound around the bobbin 601 starting at the left flange FL side of the bobbin 601 to the right flange FR side to form a first layer bottom coil 602. The coil 602, at its end, is bridged electrically at 603, as by insulated wire, to a second length of electrically conductive insulative wire that is wound in the same direction, left to right, again starting at the flange FL side to the right FR side, to form a second layer top coil 604. So, the voltage is applied across from the beginning of the first coil 602 to the end of the second coil 604. The two coils are connected in series, but overlap in a mirror image of one another. The current in the first coil 602 induces current in the second coil 604, and, simultaneously, current in the second coil 604 induces current in the first coil 602.

Figure 11:
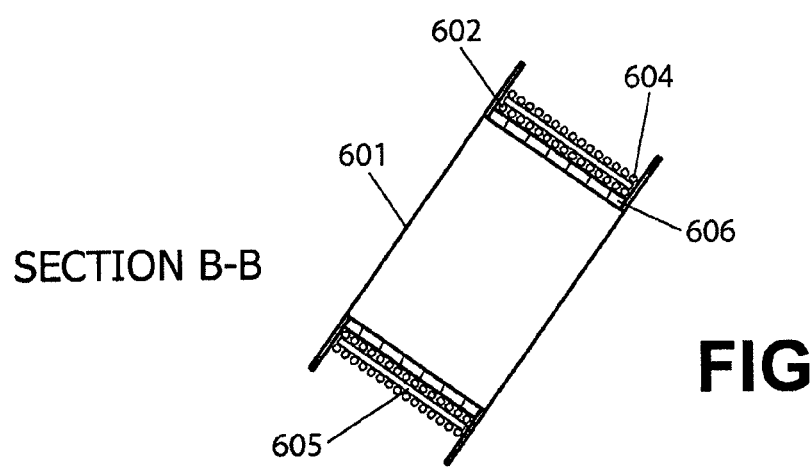
FIG. 11 is a cross-sectional view taken along the line B-B of FIG. 10.

As best seen in FIG. 11, the bottom coil 602 is insulated at 605 from the top coil 604. The bobbin 601 may be lined with a sheet of cloth material 606.

Figure 12:
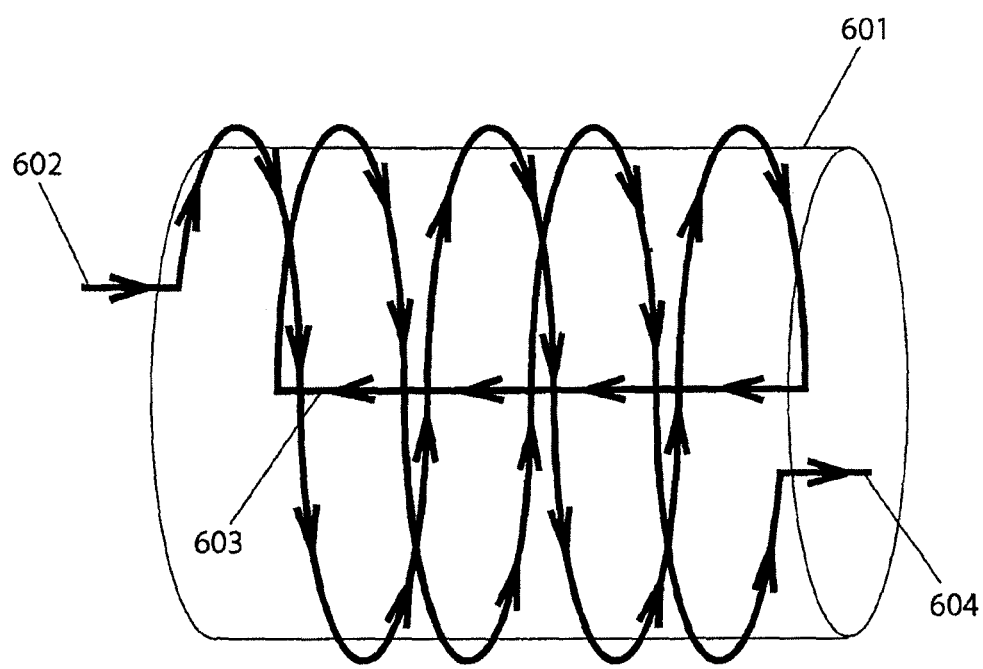
FIG. 12 is a schematic view of the pattern of the wire coils around the bobbin and the direction of current flow.

FIG. 12 is a schematic showing current direction and flow from the first coil 602, through the bridge 603 and second coil 604, in both instances moving from left to right.

Figure 13:
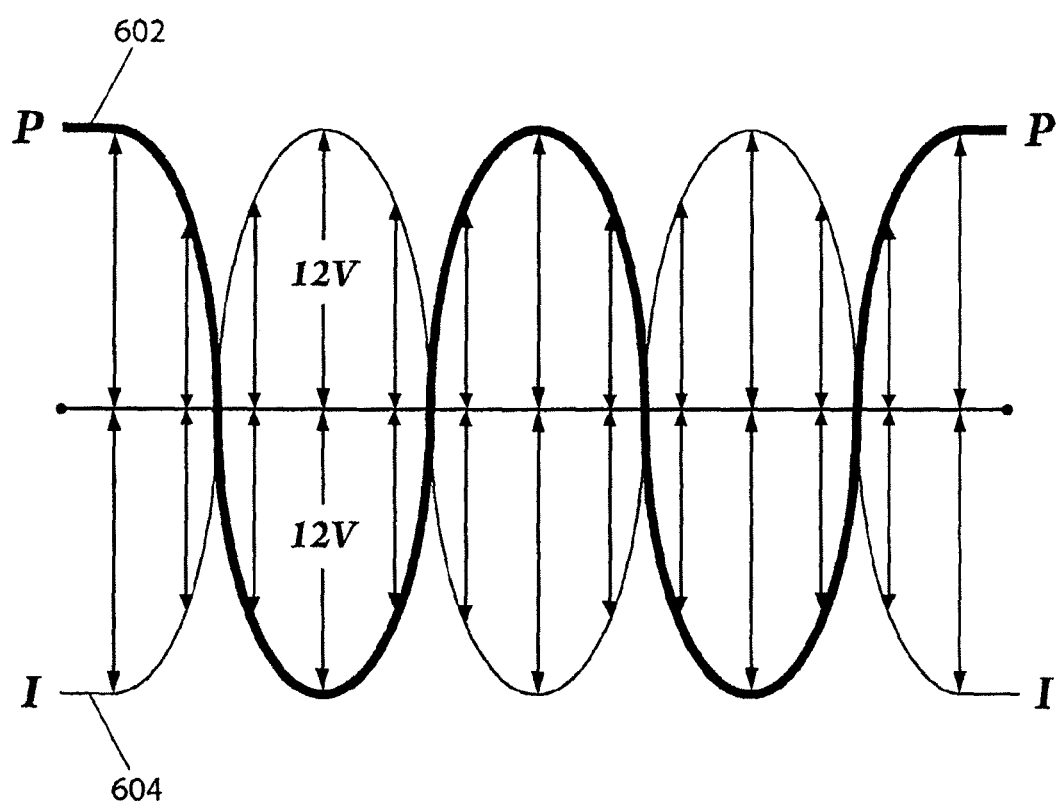
FIG. 13 is a schematic view showing the scalar waves produced in the first coil and induced in the second coil on the bobbin.

FIG. 13 is a schematic showing that when current enters the first coil 602 it induces current in the second coil 604. Likewise, though not illustrated, current in the second coil 604 induces current in the first coil 602, thereby creating a scalar effect, producing energy in the form of a helix. The waves are identical, but out of phase temporally, that is, physically identical, but 180 degrees out of phase in terms of time. It is in a helix pattern, in effect matching the DNA helix so that, it is believed, the apparatus and body are compatible and work together in harmony, producing the apparatus's effectiveness.

Although on separate bobbins, the coils 250b and 250a in the first embodiment depicted in FIGS. 2-4, are matched in the same way.

The wires forming the bottom 602 and top 604 coils are then energized in the same way as the previous embodiment to generate a magnetic field within the interior region of the bobbin 601.

Figure 14:
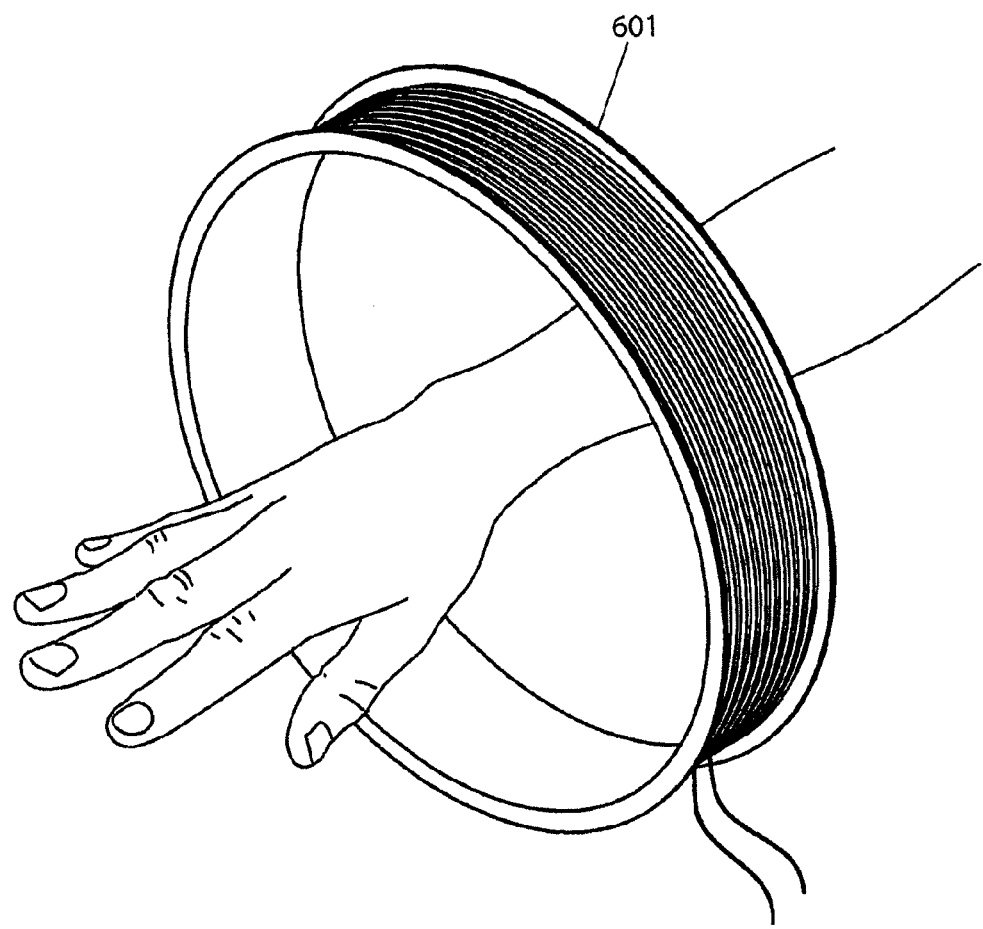
FIG. 14 is a perspective view showing the single bobbin apparatus being used on an arm.

FIG. 14 illustrates the apparatus being used on an individual with the hand placed within the interior region of bobbin 601. As with the embodiment depicted in FIGS. 2-7, a trigger may be positioned on the hand.

While various embodiments of the present invention have been described above, it should be understood that they have been presented by way of example only, and not in limitation. Accordingly, it will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A magnetic field therapy apparatus, comprising:
   a first bobbin formed of non-magnetic material having a first interior circumference and a first exterior circumference with a first radius Ra to said first interior circumference, and having a starting side and a terminating side;
   a second bobbin formed of non-magnetic material having a second interior circumference and a second exterior circumference with a second-radius Rb to said second exterior circumference, and having a starting side and a terminating side and wherein said second bobbin is concentrically confined by said first bobbin;
   said second bobbin including a hollow second bobbin interior region adapted for receipt therein of at least an appendage of a living being;
   a first length of electrically conductive insulated wire wound around said first bobbin from the first bobbin starting side to the first bobbin terminating side, to form a first coil;
   a second length of electrically conductive insulated wire wound around said second bobbin from the second bobbin starting side to the second bobbin terminating side to form a second coil, and wherein said first and second coils are electrically connected in series; and,
   an AC power unit coupled to the first and second lengths of wire for energizing said first and second coils and generating a magnetic field within said second bobbin interior region:
   wherein the difference in length of the second radius Rb of the second bobbin and the first radius Ra of the first bobbin is equal to or less than 4% of the length of the first radius Ra.

2. The apparatus according to claim 1, wherein said bobbin material is selected from the group consisting of copper and alloys thereof.

3. The apparatus according to claim 1, wherein said AC power unit is effective to produce a combined magnetic flux within said second bobbin interior region having a maximum flux density varying dependent upon desired treatment results.

4. The apparatus according to claim 3, wherein said AC power unit is adapted for connection between a source of commercially available AC power to both coils, and said adjustment mechanism includes a variable transformer.

5. The apparatus according to claim 3, further comprising a metering mechanism coupled to said adjustment mechanism for providing an indication of the power applied to at least one of said coils.

6. The apparatus according to claim 1, wherein said AC power unit includes an adjustment mechanism for varying current applied to at least one of said coils.

7. The apparatus according to claim 1, wherein an epoxy maintains a substantially uniform radial minimum distance between said first and second bobbins.

8. The apparatus according to claim 1, further comprising a layer of cloth interposed between at least one bobbin and at least one coil.

9. The apparatus according to claim 1, further comprising an electrically insulative toroidal housing enclosing at least one of said bobbins and corresponding coil.

10. The apparatus according to claim 1, further comprising at least one thermocouple for measuring temperature of at least one of said insulated wires.

11. The apparatus according to claim 1, further comprising at least one wearable magnetic trigger.

12. The apparatus according to claim 1, wherein the magnetic field within the second bobbin interior region generated by the first and second coils when they are energized by the AC power unit is in the form of a helix with identical but temporally out of phase waves of energy.

13. The apparatus according to claim 1, wherein the magnetic field within the second bobbin interior region generated by the first and second coils when they are energized by the AC power unit is in the form of physically identical, but 180 degrees out of phase in terms of time, waves of energy.

14. The apparatus according to claim 1, wherein the magnetic field within the second bobbin interior region generated by the first and second coils when they are energized by the AC power unit is scalar.

15. A method of treating of treating a biological subject comprising the steps of:
    energizing a first coil of wire wound about a first non-magnetic bobbin having a first radius Ra to an interior circumference thereof and a second coil of wire wound about a second non-magnetic bobbin concentrically confined by said first bobbin having a second-radius Rb to an exterior circumference thereof, said at least first and second coils are electrically connected in series, and are a mirror image of one another;
    generating an AC electromagnetic field component with the first and second coils substantially within an area defined by an interior region of said second bobbin; and,
    placing a biological subject in said interior region of said second bobbin and exposing said biological subject to said AC electromagnetic field,
    wherein the difference in length of the second radius Rb of the second bobbin and the first radius Ra of the first bobbin is equal to or less than 4% of the length of the first radius Ra.

16. The method of claim 15, further comprising the step of directing the energy of the AC electromagnetic field to a trigger.

17. The method of claim 15, wherein the step of energizing the first and second coils of wire further comprises the step of selecting an input current in the range of between 1 amp and 5 amps.

18. The method of claim 15, further comprising the step of generating an AC magnetic field component having a maximum flux density varying depending upon desired treatment results.

19. The method of claim 15, wherein the AC electromagnetic field component is in the form of a helix with identical but temporally out of phase waves of energy.

20. The method of claim 15, wherein the AC electromagnetic field component is in the form of physically identical, but 180 degrees out of phase in terms of time, waves of energy.

21. The method of claim 15, wherein the AC electromagnetic field component is scalar.

22. A therapy apparatus, comprising:
    a first bobbin formed of non-magnetic material having a first interior circumference with a first radius Ra to said first interior circumference, and having a starting side and a terminating side;
    a second bobbin formed of non-magnetic material having a second exterior circumference with a second-radius Rb to said second exterior circumference, and having a starting side and a terminating side and wherein said second bobbin is concentrically confined by said first bobbin, the second bobbin including a hollow interior region adapted for receipt therein of at least an appendage of a user;
    a first length of electrically conductive insulated wire wound around said first bobbin from the first bobbin starting side to the first bobbin terminating side, to form a first coil;
    a second length of electrically conductive insulated wire wound around said second bobbin from the second bobbin starting side to the second bobbin terminating side to form a second coil, and wherein said first and second coils are electrically connected in series; and,
    an AC power unit coupled to the first and second lengths of wire for energizing said first and second coils and generating a scalar magnetic field in the form of a helix with physically identical but temporally out of phase waves of energy within the hollow interior region of the second bobbin,
    wherein the difference in length of the second radius Rb of the second bobbin and the first radius Ra of the first bobbin is equal to or less than 4% of the length of the first radius Ra.

* * * * *